United States Patent [19]
Roreger

[11] Patent Number: 6,117,437
[45] Date of Patent: Sep. 12, 2000

[54] PHARMACEUTICAL FORM FOR DELIVERY OF ACTIVE SUBSTANCES TO WOUNDS

[75] Inventor: Michael Roreger, Neuwied, Germany

[73] Assignee: LTS Lohmann Therapie-Systeme GmbH, Neuwied, Germany

[21] Appl. No.: 08/875,725

[22] PCT Filed: Jan. 25, 1996

[86] PCT No.: PCT/EP96/00295

§ 371 Date: Sep. 18, 1997

§ 102(e) Date: Sep. 18, 1997

[87] PCT Pub. No.: WO96/23488

PCT Pub. Date: Aug. 8, 1996

[30] Foreign Application Priority Data

Feb. 2, 1995 [DE] Germany .......................... 195 03 336

[51] Int. Cl.$^7$ .......................... A61K 31/74; A01N 25/34
[52] U.S. Cl. .................. 424/404; 424/78.02; 424/78.03; 424/402; 424/449; 424/490; 424/494
[58] Field of Search .............................. 424/78.02, 78.03, 424/402, 404, 449, 490, 494

[56] References Cited

U.S. PATENT DOCUMENTS 4,834,978 5/1989 Nuwayser ................................ 424/448
5,098,417 3/1992 Yamazaki et al. ...................... 604/304

FOREIGN PATENT DOCUMENTS 0 049 177 4/1982 European Pat. Off. .
1 190 608 4/1965 Germany .

*Primary Examiner*—Jose' G. Dees
*Assistant Examiner*—Kathryne E. Shelborne
*Attorney, Agent, or Firm*—Wenderoth, Lind & Ponack, L.L.P.

[57] ABSTRACT

A pharmaceutical form for delivery of active substances to wounds is characterized in that this is designed to be coherent, sheet-like and, in its extent in terms of area, equal to or smaller than the wound area to be managed, and contains active substance in a defined amount in homogeneously dispersed form.

18 Claims, No Drawings

PHARMACEUTICAL FORM FOR DELIVERY OF ACTIVE SUBSTANCES TO WOUNDS

BACKGROUND OF THE INVENTION

In the treatment of wounds, it is necessary for active substances which are intended or need to come into direct contact with the surface of the wound or the bottom of the wound to be administered by means of pharmaceutical forms which, by reason of their consistency, can be applied without gaps even to very uneven surfaces. This normally takes place with the aid of solutions, powders, dusting powders, sprays, semisolid preparations, such as ointments, creams and gels. The disadvantages of these pharmaceutical forms become clear, in particular, when it is necessary to give doses of highly active substances in a small amount, accurately and reproducibly, or when controlled release from the pharmaceutical form is desirable for the therapy to maintain a uniform concentration of active substance in the wound throughout a particular period.

Wound dressings which, by reason of their composition and their structure, are loaded with active substances and release the latter in a delayed or controlled manner are described, for example, in U.S. Pat. No. 5,098,417, in EP 49 177 or in DE-B 11 90 608. These wound dressings have the disadvantage that, especially in the case of deep wounds, they do not come into contact with the bottom of the wound. The ability of such wound dressings to function is, moreover, greatly dependent on the interaction with wound fluid, since, the release can take place only by diffusion of the active substance at the interface between wound dressing and wound fluid or by erosion of the active substance from the wound dressing after uptake of fluid and swelling of the carrier material. Since the fluid conditions in wounds vary greatly between individuals and depending on the type of wound and phase of wound healing, it is not possible to achieve comparable and reproducible kinetics of release with such wound dressings in vivo.

BRIEF DESCRIPTION OF THE INVENTION

The present of the present invention is based on the object of forming a pharmaceutical form which, on the one hand, permits an accurate and reproducible dose of active substance to be given and the release of active substance to be controlled reliably and which, on the other hand, corresponding to the traditional pharmaceutical forms mentioned at the outset, can be adapted to uneven wound surfaces even with deep wounds and can be brought into contact therewith. It has surprisingly been found that this is achieved by a deformable, sheet-like pharmaceutical form which delivers active substance, is coherent and is designed to be in its sheet-like extent equal to or smaller than the wound area to be managed and which contains the active substance in defined amounts in homogeneously dispersed form. Further embodiments of the pharmaceutical form are described below.

Conventional deformable pharmaceutical forms which deliver active substance and which, after application into the wound, form sheet-like structures such as, for example, gels, ointments, creams or else liquid multicomponent systems which, after mixing in the wound, react together with solidification, belong, according to the specialist terminology, to the so-called multiple dose pharmaceutical forms. This means that the amount of the pharmaceutical form present in one container is intended for a plurality of uses with appropriate dosing procedures. The dosage itself is performed by the individual user. The user is able to make statements about the amount of active substance in the dose only if he weighs the particular dose before use. On repeated use, reproducible application of a constant amount of active substance would be possible only with the aid of a weighing procedure beforehand. This individually variable dosage is possible only because of the low coherence and easy divisibility of these pharmaceutical forms. On the other hand, the low coherence has the advantage that the pharmaceutical form can be, as mentioned, deformed as required and can be adapted to uneven surfaces.

By contrast, the pharmaceutical form according to the invention is a single dose pharmaceutical form which, similar to tablets or capsules, is coherent and preshaped and contains a defined dose of active substance for one use in homogeneously dispersed form. This has the advantage that a predetermined amount of active substance can be administered as often as required and reproducibly.

Coherence means in this connection a firmness and an internal cohesion of the pharmaceutical form which, in contrast to the conventional pharmaceutical forms described, permits manipulation by the user such that the preset amount of pharmaceutical form and thus the given amount of active substance is not automatically determined, altered or influenced by the manipulation itself.

The pharmaceutical form according to the invention differs from other single dose pharmaceutical forms, such as, for example, tablets or capsules, in that although, on the one hand, it has the coherence necessary for manipulation, on the other hand it is flexible and deformable so that it can, after introduction into the wound, be adapted to the irregularities of the bottom of the wound and can be brought into contact with the latter. The precondition for this is that the sheet-like extent of the pharmaceutical form is less than or not more than equal to the wound area to be managed. Similar to the solid pharmaceutical forms mentioned, the homogeneity of dispersion of the active substance is achieved by initially preparing a complete composition of the ancillary components in which the active substance is homogeneously dispersed. Normally, during the course of the process of making the pharmaceutical form, a plurality of divided pharmaceutical forms of the same shape and same weight, all of which accordingly have the same content of active substance, is produced from such a composition. Typically, a consolidation which confers coherence on the divided individual pharmaceutical form takes place during the making of the pharmaceutical form by physical means, for example exertion of pressure, or chemical reactions.

DETAILED DESCRIPTION OF THE INVENTION

To produce a pharmaceutical form according to the invention, first a low-viscosity, free-flowing composition is prepared, for example a solution, a dispersion or a melt, which contains active substance in homogeneously dispersed form. This composition is then coated onto a flat substrate by processes known to the skilled person. In contrast to the solid pharmaceutical forms mentioned, in the production of a pharmaceutical form according to the invention the consolidation procedure which confers the coherence on the individual divided pharmaceutical form takes place not during the procedure of making and dividing the pharmaceutical forms but beforehand. The consolidation takes place after the coating onto a flat substrate by removing the dissolving or dispersing medium by drying or by cooling if a melt has been used for coating. The buildup of cohesive forces which takes place during this depends in nature and strength on the composition of the ancillary substances. The result is a wide, sheet-like continuous belt with a thickness which is predetermined by the coating. The limiting factor for the thickness of the band is, for a given formulation, the requirement for flexibility and deformability of the individual divided pharmaceutical form for adaptation to the bottom of the wound after introduction into a wound. Individual pharmaceutical forms with a predetermined area are divided out of the endless belt by known processes, such as, for example, punching and cutting. Since the coating is carried out with a composition which contains active substance in homogeneously dispersed form and maintenance of a constant coating weight, all the individually divided pharmaceutical forms contain the same amount of active substance in homogeneous dispersion. This makes accurate and reproducible dosage by the user possible. Since the content of active substance per unit area and area itself can be varied continuously over a wide range by the production process, the pharmaceutical form according to the invention provides the possibility of accurate and reliable dosage of even very small amounts of active substance. Furthermore, the user is able to dose the active substance based on the particular problem and the therapeutic requirements. Thus, the user is able, for example, to introduce a plurality of pharmaceutical forms simultaneously into the wound and apply them side by side to the bottom of the wound. However, the user is also able to divide off small pieces from a pharmaceutical form of given area if, for example, the wound area to be treated is smaller than the extent in terms of area of the pharmaceutical form, or if the dose of active substance in the pharmaceutical form given by the area is too high for a specific treatment. Thus, the pharmaceutical form according to the invention can, for example, be provided to the user in conjunction with an inert sheet-like substrate from which the pharmaceutical form can easily be detached, such as, for example, a siliconized sheet, the latter possibly having divisions on the cm scale. Since the surface loading of the pharmaceutical form with active substance is known, the user is able to cut the area, and thus the amount of active substance which he regards as necessary from the therapeutic viewpoint, out of or off from the pharmaceutical form which is in the form of a sheet or rolled-up strip.

In each case, the result is that the sheet-like extent of the pharmaceutical form is less than or not more than equal to the wound area to be managed. This makes application to the bottom of the wound possible and ensures that the amount of active substance administered is released in the wound. On application overlapping the edges of the wound, only the part of the pharmaceutical form extending into the wound would release active substance, which would cancel out the advantage of accurate dosage.

Active substances which are used in the pharmaceutical forms according to the invention in wounds are preferably haemostatic active substances, wound-cleansing active substances such as, for example, enzymes, antiseptics, disinfectants and antibiotics, and active substances which promote wound healing and which stimulate granulation, induce neoangiogenesis or promote epithelization.

Increasingly important active substances which promote wound healing are biologically active peptides and proteins which even in very low concentration display high activities and most of which are produced by recombinant technologies. The pharmaceutical form according to the invention represents a particularly suitable carrier and delivery system for these substances, which include so-called growth factors such as platelet derived growth factor (PDGF), epidermal growth factor (EDF), platelet derived endothelial cell growth factor (PD-ECGF), acidic fibroblast growth factor (aFGF), basic fibroblast growth factor (bFGF), transforming growth factor α (TGFα), transforming growth factor β (TGFβ), keratinocyte growth factor (KGF), insulin-like growth factors 1 and 2 (IGF1 IGF2) and tumour necrosis factor (TNF).

Another advantage of the pharmaceutical form according to the invention is that controlled release of active substance therefrom is possible. Since the pharmaceutical form always comes into contact with wound or tissue fluid after application, the interaction with fluid has a crucial effect on the release of active substance, which can in turn be utilized to control the release. Thus, the formula of the pharmaceutical form according to the invention can, in order to achieve relatively rapid release of active substance, be designed so that the pharmaceutical form is soluble or able to disintegrate in wound fluid. The kinetics of release of active substance depend in this case on the rate of dissolution or disintegration of the pharmaceutical form. After the application time has elapsed, the dissolved or disintegrated pharmaceutical form must, similar to ointments or creams, be washed out of the wound, unless the formula is designed so that the pharmaceutical form can be completely broken down and absorbed in wound fluid as far as the molecular range of the individual components. Release of active substance can be delayed and prolonged by choosing the composition so that the pharmaceutical form merely swells on uptake of wound fluid. The wound fluid in particular dissolves the active substance out of the pharmaceutical form, which leads to slow erosion of the latter. In this case, the release of active substance depends on the swelling capacity and the rate of erosion of the pharmaceutical form.

Release of active substance is delayed and prolonged even further by choosing the composition of the pharmaceutical forms so that it is inert to wound fluid and does not interact therewith. The kinetics of release of active substance then depend only on the rate of diffusion of active substance within the pharmaceutical form and at the interface between pharmaceutical form and floor of the wound or wound fluid.

In the cases mentioned, in which the pharmaceutical form is not soluble or able to disintegrate, the user has the advantage that he can remove it completely from the wound at any time without washing out or similar manipulations.

In another preferred embodiment, the pharmaceutical form according to the invention has a multilayer structure. Thus, for example, a layer which is soluble or able to disintegrate in wound fluid and which serves for rapid release of active substance for the minimum necessary concentration of active substance to be reached as quickly as possible can be combined in laminate form with a swellable or an inert layer which serves for slow and uniform release of active substance to maintain the necessary concentration of active substance over a lengthy period. Multilayer pharmaceutical forms of this type can also be used if, for example, the release of different active substances is to take place at different times or with different rates of release.

In a preferred embodiment of a multilayer pharmaceutical form, this comprises a barrier and/or control element which contains no active substance such as, for example, a flexible sheet of polyurethane, polyester or polypropylene. The intention of such a barrier or control element is to direct delivery of active substance in a particular direction. If, for example, a deformable layer which delivers active substance is applied to the bottom of the wound, a barrier layer laminated thereon is able to prevent, for example in a wound with heavy exudation, active substance being delivered to the surrounding wound fluid, which might possibly lead to an undesirably great dilution effect. A pharmaceutical form according to the invention with barrier element proves to be particularly advantageous, for example, when bacterial colonies located in mixtures in the floor of the wound in cases of infection are to be controlled rapidly and in high concentration with antiseptics or antibiotics.

In another preferred embodiment of the pharmaceutical form according to the invention for wound treatment, the latter is porous, for example foam- or sponge-like. The size of the pores and the structure of the pharmaceutical form is designed so that cells such as, for example, fibroblasts are able to migrate into it and, at the same time, a structural orientation is given to the cells, which is attributable in particular to the degree of order, which is preferably similar to natural connective tissue, of the sponge structure in the pharmaceutical form. Ingrowth of cells may, for example, be necessary for breakdown of the preparation or for the delivery or deposit of substances which, for example, are needed for new tissue formation or for vascularization of a tissue which is to replace the pharmaceutical form according to the invention after breakdown thereof. The preconditions for porosity of the pharmaceutical form would in this case be produced during production by, for example, introducing air into the composition which is to be coated and which has a homogeneous dispersion of active substance, or by holes or pores being left in the coated web by the evaporating solvent or dispersing medium due to external drying conditions after coating from the solution or dispersion. The selection of materials and ancillary substances for producing the pharmaceutical form according to the invention is primarily determined by the requirement of its coherence, flexibility and deformability and by requirements for the required kinetics of release of active substance. Another restricting factor is that the range of materials and ancillary substances which can be used is reduced to those which display excellent tolerability on contact with wound tissue. The pharmaceutical form produced from a combination of materials and ancillary substances ought, after application into the wound, not impede the function and activity of cells such as, for example, keratinocytes, fibroblasts or endothelial cells.

The minimum necessary for producing a pharmaceutical form according to the invention are ancillary substances from the group of polymers and ancillary substances from the group of plasticizers. Polymers ensure the internal cohesion and the coherence of the pharmaceutical form because, after coating and drying or cooling, they form, through, for example, covalent bonds, hydrogen bonds or ionic interactions, networks which serve for consolidation and thus provide the necessary coherence to the pharmaceutical form. Plasticizers adjust the consistency of the pharmaceutical form so that it is flexible and deformable and thus can be adapted to the floor of the wound. Suitable plasticizers with physiological suitability for wound treatment are preferably low molecular weight polyhydric alcohols such as, for example, glycerol, sorbitol, low molecular weight polyethylene glycol or low molecular weight polypropylene glycol.

Polymers suitable for a rapid-release device which is soluble, or at least disintegrates, in wound fluid are, in particular, water-soluble polymers. These preferably include collagen and gelatin, vegetable polysaccharides such as alginates, pectins, carrageenans or xanthan, cellulose derivatives such as methylcellulose, hydroxypropylcellulose, hydroxyethylcellulose, hydroxypropylmethylcellulose or sodium carboxymethylcellulose, starch and starch derivatives, galactomannan and galactomannan derivatives, chitosan and chitosan derivatives, glycoproteins, proteoglycans, glucosaminoglycans, polyvinyl alcohol, polyvinylpyrrolidone, vinylpyrrolidone/vinyl acetate copolymers, high molecular weight polyethylene glycols and high molecular weight polypropylene glycols.

Polymers suitable for a pharmaceutical form with delayed release over a lengthy period, which swells in wound fluid or does not interact with wound fluid, are, in particular, polymers which are swellable in water or insoluble in water. These preferably include cellulose derivatives such as ethylcellulose, cellulose acetate phthalate, hydroxypropylmethylcellulose phthalate, cellulose acetate succinate or ethylcellulose succinate, polyoxyethylene/polyoxypropylene copolymers, polyvinyl alcohol, polyacrylates and polymethacrylates, polylactides, polyglycolides and polyamino acids.

The pharmaceutical may contain the following as further ancillary substances:

preservatives such as, for example p-Cl-m-cresol, phenylethyl alcohol, phenoxyethyl alcohol, chlorobutanol, methyl 4-hydroxybenzoate, propyl 4-hydroxybenzoate, benzalkonium chloride, cetylpyridinium chloride, chlorhexidine diacetate or digluconate, ethanol or propylene glycol pH regulators such as, for example, glycine buffer, citrate buffer, borate buffer, phosphate buffer or citric acid/phosphate buffer antioxidants such as, for example, ascorbic acid, ascorbyl palmitate, tocopherol acetate, propyl gallate, butylhydroxyanisole or butylhydroxytoluene, ancillary substances to stabilize the biological activity of active substances such as mannitol, glucose, lactose, fructose, sucrose, cyclodextrin or dextran, emulsifiable ancillary substances such as oils, fats and waxes, emulsion stabilizers such as, for example, nonionic emulsifiers, amphoteric emulsifiers, cationic emulsifiers and anionic emulsifiers, bulking agents such as, for example, microcrystalline cellulose, aluminium oxide, zinc oxide, titanium dioxide, talc, silicon dioxide, magnesium silicate, magnesium aluminium silicate, kaolin, hydrophobic starch, calcium stearate or calcium phosphate, foaming agents such as saponins, alginic esters, amine oxides or fatty amine oxides.

EXAMPLE 1

34 g of acetone, 6 g of polyethylene glycol 400 and 16 g of ethyl acetate are introduced into a stirring vessel which can be closed. While stirring at a constant speed, 33.6 g of a polyvinylpyrrolidone/polyvinyl acetate copolymer, 2 g of a polyoxyethylene/polyoxypropylene copolymer and 3.3 g of hydroxypropylcellulose are successively dissolved in the solvent mixture.

EXAMPLE 2

3.3 g of lidocaine are dissolved in the stock solution of Example 1 while stirring at a constant speed. The solution is coated with a coat thickness of 300 $\mu$m on siliconized paper and dried convectively in a drying channel at 50° C. with an air speed of about 5 m/sec. Drying results in a soft, slightly cloudy, flexible film which has a weight per unit area of 130 g/m$^2$ and accordingly has an active substance content of 0.8 mg of lidocaine/cm$^2$.

Circular pharmaceutical forms with an area of 5 cm² and, accordingly, an active substance content of 4 mg of lidocaine are punched out of the film. The pharmaceutical forms are each placed in a paddle-over-disc apparatus and stirred in 500 ml of demineralized water at 50 rpm and 32° C. 10 ml portions of the released medium are removed after 30 minutes, 1, 2, 4 and 24 hours. The amount of active substance released is determined by HPLC. Result:

| Removal time | Amount of active substance released (in mg; cumulative) |
| --- | --- |
| 30 min | 3.1865 |
| 1 hour | 3.4828 |
| 2 hours | 3.7978 |
| 4 hours | 3.8807 |
| 24 hours | 4.1102 |

The pharmaceutical form has disintegrated into several small pieces after 30 min; the release of active substance from the pharmaceutical form at this time is already almost 80% and is 97% after 4 hours. The desired requirements for this type of pharmaceutical form, rapid release of active substance to achieve rapid alleviation of pain and maximal utilization of the active substance administered, are met.

EXAMPLE 3

5.2 g of chlorhexidine hydrochloride are dissolved in the stock solution of Example 1 while stirring at a constant speed. The solution is coated on siliconized paper and dried under the same conditions as in Example 2. The resulting soft, deformable film has a weight per unit area of 130 g/m² and, accordingly, an active substance content of 1.2 mg of chlorhexidine hydrochloride/cm². Circular pharmaceutical forms with an area of 5 cm² and, accordingly, an active substance content of 6 mg of chlorhexidine hydrochloride are punched out of the film. The pharmaceutical forms are each placed in a paddle-over-disc apparatus and stirred in 500 ml of demineralized water at 50 rpm and 32° C. 10 ml portions of the release medium are removed after 30 minutes and one hour. The amount of active substance released is determined by HPLC. Result:

| Removal time | Amount of active substance released (in mg; cumulative) |
| --- | --- |
| 30 min | 6.1400 |
| 1 hour | 6.1963 |

The pharmaceutical form has completely disintegrated after 30 minutes, and 100% of the amount of active substance administered is released. On use, the antiseptic effect of the chlorhexidine hydrochloride would have a very rapid and highly concentrated onset, which is also necessary for infections. Utilization of the active substance introduced is optimal.

EXAMPLE 4

34 g of acetone, 16 g of ethyl acetate and 6 g of polyethylene glycol 400 are introduced into a stirred apparatus which can be closed. While stirring at a constant speed, 6 g of ethylcellulose, 11 g of a polyvinylpyrrolidone/polyvinyl acetate copolymer, 5.5 g of hydroxypropylcellulose, 1 g of polyoxyethylene/polyoxypropylene copolymer and 0.9 g of oestradiol are successively dissolved in the solvent mixture.

The solution is coated with a coat thickness of 400 μm on siliconized paper and dried convectively in a drying channel at 50° C. with an air speed of about 5 m/sec. Drying results in a soft, deformable film which has a weight per unit area of 130 g/m² and, accordingly, an active substance content of 0.385 mg of oestradiol/cm². This film differs from those described in Examples 2 and 3 in that it is necessary, in order to achieve an effect promoting wound healing by administration of oestradiol, for release of an initial dose of this active substance optimally to be followed by continuous and controlled release over a lengthy period of a low-dose maintenance dose.

To investigate the kinetics of release, circular pharmaceutical forms with an area of 5 cm² and an active substance content of 1.924 mg of oestradiol are punched out of the film. The devices are each placed in a paddle-over-disc apparatus and stirred in 500 ml of demineralized water at 50 rpm and 32° C. 10 ml portions of the release medium are removed after 30 minutes and 2, 6 and 24 hours. The amount of active substance released is determined by HPLC.

| | Result: |
| --- | --- |
| Removal time | Amount of active substance released (in mg; cumulative) |
| 30 minutes | 0.9957 |
| 2 hours | 1.0943 |
| 6 hours | 1.1814 |
| 24 hours | 1.3079 |

After 30 minutes, the pharmaceutical form shows moderate swelling; about half the amount of active substance administered has been released. The results show that the release of active substance is subsequently distinctly reduced and about 10–20 μg of oestradiol per hour are delivered as maintenance dose. 68% of the amount of active substance administered are released after 24 hours. The active substance reservoir in the pharmaceutical form, which also disintegrates after several hours, is sufficient for continuous, low-dose oestradiol release to be possible even on use for several days.

I claim:

1. A wound-treating pharmaceutical composition in a polymer-based foil or flat-shaped form of uniform thickness and consistency, which delivers a pharmaceutically active substance to a wound, wherein said composition:

comprises at least one pharmaceutically active substance which is homogeneously dispersed in the composition and is present in an application-related concentration per unit area;

allows the controlled release of said active substance to the wound's surface in an effective amount per surface area;

is coherent and has a flexibility to match the wounds surface; and the concentration of the active substance and the release thereof corresponds to the treatment of the wound, with an area of the foil or flat-shaped form being less than or, at most, equal to the wound's area, applicable to the wound as one piece corresponding to the area of the wound which can, before administration, be cut individually to the area of the particular wound to make introduction into the wound possible or as several smaller pieces.

2. The pharmaceutical composition according to claim 1, wherein the composition is in several pieces and can be introduced in a plurality of small pieces into the wound.

3. The pharmaceutical composition according to claim 1, wherein the composition is in one piece and can, before administration, be cut individually to the area of the particular wound to make introduction into the wound possible.

4. The pharmaceutical composition according to claim 1, wherein the composition comprises agents for the controlled release of the active substance.

5. The pharmaceutical composition according to claim 1, wherein the composition is soluble in or able to disintegrate in the wound fluid, with the kinetics of release of active substance depending on its rate of dissolution or disintegration.

6. The pharmaceutical composition according to claim 1, wherein the composition can be broken down and absorbed in wound fluid.

7. The pharmaceutical composition according to claim 1, wherein the composition is able to swell in wound fluid, with the kinetics of release of the active substance depending on the rate of erosion of the pharmaceutical composition.

8. The pharmaceutical composition according to claim 1, wherein the composition is inert to wound fluid, and the kinetics of release of active substance depends only on the rate of diffusion of the active substance.

9. The pharmaceutical composition according to claim 1, having a multi-layer structure.

10. The pharmaceutical composition according to claim 1 or 9, having at least one barrier and/or control element, to direct the delivery of active substance in a particular direction.

11. The pharmaceutical composition according to claim 1, further comprising at least one ancillary substance selected from polymers which influence the rate of release of the active substance or plasticizers.

12. The pharmaceutical composition according to claim 1 or 11, wherein the composition comprises at least one water-soluble polymer.

13. The pharmaceutical composition according to claim 11, wherein the composition comprises at least one polymer which is swellable in water and/or is insoluble in water.

14. A process for the production of a pharmaceutical composition for the delivery of active substances to a wound comprising homogeneously dispersing at least one active substance in a low viscosity, free flowing composition, solution, dispersion or melt of a film-forming material;

coating the composition, solution, dispersion or melt onto a substrate;

drying the composition, solution or dispersion to remove any dissolving or dispersing medium, or in the case of the melt, cooling the melt, to form a flat material on the substrate having a thickness of the coating, cutting or punching the material on the substrate to form a pharmaceutical composition having the same shape and weight, wherein the substrate is removable from the pharmaceutical composition prior to administration to the wound.

15. A process for treating a wound comprising placing the pharmaceutical composition according to claim 1, completely into the wound without overlapping the edges of the wound.

16. A wound-treating pharmaceutical composition in a polymer-based foil or flat shape form of uniform thickness and consistency, which delivers a pharmaceutically active substance to a wound wherein said composition: comprises at least one pharmaceutically active substance, which is homogeneously dispersed within the composition and is present in an application-related concentration per unit area;

allows the controlled release of said active substance to the wound's surface in an effective amount per surface area;

is coherent and has a flexibility to match the wound's surface;

wherein the composition is soluble in the wound fluid, disintegrate in the wound fluid or swells in the wound fluid to release said pharmaceutically active substance, and wherein the foil or flat shape form has an area equal to or less than the area of the wound.

17. A wound-treating pharmaceutical device comprising the pharmaceutical composition of claim 16.

18. The wound-treating pharmaceutical device of claim 17, which comprises multiple layers wherein the layer adjacent to the wound contains said pharmaceutical composition.

* * * * *